United States Patent [19]

Homeier

[11] 4,430,513
[45] Feb. 7, 1984

[54] ALKYLATION OF AMINE COMPOUNDS
[75] Inventor: Edwin H. Homeier, Maywood, Ill.
[73] Assignee: UOP Inc., Des Plaines, Ill.
[21] Appl. No.: 297,909
[22] Filed: Aug. 31, 1981
[51] Int. Cl.³ .................... C07C 85/02; C07C 85/00
[52] U.S. Cl. .................................. 564/469; 564/467; 564/470
[58] Field of Search ........................ 564/470, 467, 469
[56] References Cited
U.S. PATENT DOCUMENTS

| 2,542,747 | 2/1951 | Barrick | 564/467 X |
| 3,234,283 | 2/1966 | Finch et al. | 564/470 |
| 3,239,519 | 3/1966 | Winberg | 564/470 X |
| 3,264,354 | 8/1966 | Sawyer | 564/469 |
| 3,767,709 | 10/1973 | Fenton | 564/470 |
| 4,059,640 | 11/1977 | Goetz | 564/470 |
| 4,250,115 | 2/1981 | Imai | 564/467 X |

FOREIGN PATENT DOCUMENTS

| 488764 | 12/1952 | Canada | 564/469 |
| 1257783 | 1/1968 | Fed. Rep. of Germany | 564/469 |

Primary Examiner—John Doll
Attorney, Agent, or Firm—James R. Hoatson, Jr.; Raymond H. Nelson; William H. Page, II

[57] ABSTRACT

Alkylamine compounds which contain at least two alkyl substituents containing from about 2 to about 6 carbon atoms may be alkylated at temperatures ranging from about 50° to about 300° C. and pressures ranging from about 20 to about 300 atmospheres in the presence of a metal carbonyl or a metal compound capable of forming a carbonyl at reaction conditions.

11 Claims, No Drawings

ALKYLATION OF AMINE COMPOUNDS

BACKGROUND OF THE INVENTION

The alkylation of various organic compounds utilizing alkylating agents such as olefins or alkyl halides is well known in the art. The alkylation of these organic compounds, one example being the treatment of an aromatic hydrocarbon such as benzene with an olefin, is accomplished by utilizing Friedel Crafts catalysts. The type of catalyst which may be employed for the reaction will comprise a Bronstead type acid such as phosphoric acid, sulfuric acid, solid phosphoric as hydrofluoric acid, etc. or a Lewis type acid such as aluminum chloride, boron trifluoride, zinc chloride, ferric chloride, etc. As was hereinbefore mentioned, the alkylating agents which are usually employed will comprise an olefinic compound or an alkyl halide. In some instances, it may have been useful to employ an alkylamine as the alkylating agent. However, the presence of amino-nitrogen functionalities in this type of compound was detrimental to the use of such a compound due to the fact that the rate of production of the desired alkylated product proceeded at a low rate which slowed, or in some instances, ceased to operate. The low rate of reaction or inability to act as an alkylating agent thus rendered the use of such an alkylating agent economically unfeasible. The slowness of the reaction is due to the fact that the amine group of the alkylating agent poisons the catalyst by the formation of an acid-base compound, the poison thus rendering the catalyst incapable of operating as such.

As will hereinafter be shown in greater detail, it has now been discovered that an alkylamine may function as an alkylating agent in the presence of certain metal catalysts.

BRIEF SUMMARY OF THE INVENTION

This invention relates to the alkylation of alkylamine compounds. More specifically, the invention is concerned with the alkylation of an alkylamine in the presence of certain metal carbonyl catalysts which will retain their activity and ability to catalyze the aforesaid alkylation during the desired reaction period.

Alkylamine compounds which contain at least two alkyl substituents have been found to undergo what, for the purposes of this invention, may be termed a self-alkylation reaction in which one of the alkyl substituents acts as an alkylating agent. The alkylated amines which are formed by the present reaction and which will constitute amines containing alkyl substituents of dissimilar lengths may be utilized as intermediates in the preparation of disinfectants and detergents as well as be used in the rubber industry or as catalyst modifiers in other organic reactions such as hydroformylation reactions in which an olefinic hydrocarbon is converted to an alcohol containing one more carbon atom than the olefinic compound by treatment with carbon monoxide and hydrogen in the presence of a metallic catalyst such as a rhodium compound and the aforesaid catalyst modifier.

It is therefore an object of this invention to provide a process for the alkylation of an alkylamine compound.

A further object of this invention is to provide a process for the alkylation of an alkylamine containing at least two alkyl substituents utilizing certain metal carbonyl compounds as catalysts.

In one aspect, an embodiment of this invention resides in a process for the alkylation of an amine compound containing at least two alkyl substituents which comprises treating said compound at alkylation conditions in the presence of a cobalt or rhodium containing compound which is capable of forming a carbonyl under alkylation conditions, and recovering the resultant alkylated amine product.

A specific embodiment of this invention is found in a process for the alkylation of an amine compound which comprises treating triethylamine at a temperature in the range of from about 50° C. to about 300° C. and a pressure in the range of from about 20 to about 300 atmospheres in a carbon monoxide and hydrogen atmosphere in the presence of a catalyst comprising dicobalt octacarbonyl and recovering a mixture of butyldiethylamine, hexyldiethylamine, octyldiethylamine, decyldiethylamine and dodecyldiethylamine.

Other objects and embodiments will be found in the following further detailed description of the present invention.

DETAILED DESCRIPTION OF THE INVENTION

As hereinbefore set forth, the present invention is concerned with a process for the alkylation of amine compounds. The reaction is effected by treating an alkylamine containing at least two alkyl substituents in a carbon monoxide and hydrogen atmosphere with a metal carbonyl catalyst, and particularly a cobalt carbonyl or rhodium carbonyl catalyst. The alkylation reaction is effected at alkylation conditions which will include a temperature in the range of from about 50° up to about 300° C. or more and a pressure which may range from about 20 to about 300 atmospheres or more. The aforementioned superatmospheric pressures are effected by the presence of a carbon monoxide and hydrogen atmosphere in which the two gases may be present in a mole ratio which may range from about 0.1:1 to about 1000:1 moles of carbon monoxide per mole of hydrogen.

The alkylamine compounds which will undergo alkylation according to the process of this invention will comprise alkylamines containing at least two alkyl substituents such as dialkylamine and trialkylamine. In the preferred embodiment of the invention, the alkyl group will contain from about 2 to about 6 carbon atoms, some specific examples of these alkylamine compounds being diethylamine, di-n-propylamine, di-isopropylamine, di-n-butylamine, di-t-butylamine, di-n-pentylamine, di-sec-pentylamine, di-n-hexylamine, di-sec-hexylamine, triethylamine, tri-n-propylamine, tri-n-butylamine, tri-t-butylamine, tri-n-pentylamine, tri-sec-pentylamine, tri-n-hexylamine, tri-sec-hexylamine, etc.

The catalysts which are used to effect the alkylation reaction and which are not poisoned by the formation of an acid-based compound will comprise metal carbonyls or compounds capable of forming a carbonyl under alkylation conditions. Some specific examples of these metal catalysts will include cobalt chloride, cobalt bromide, cobalt nitrate, dicobalt octacarbonyl, tetracobalt dodecacarbonyl, cobalt carbonyl acetylacetonate, rhodium chloride, rhodium carbonyl chloride, tetrarhodium dodecarbonyl, etc. It is to be understood that the aforementioned compounds are merely illustrative, and that other metal compounds may also be used, although not necessarily with equivalent results.

The process of the instant invention may be accomplished in either a batch or continuous type operation. For example, when a batch type operation is to be employed, a quantity of the catalyst and amine compound which contains at least two alkyl substituents along with an organic solvent, if one is to be used, will be placed in a pressure-resistant apparatus such as an autoclave of the stirring, mixing or rotating type. The solvents which may be employed in the present invention may comprise paraffins such as pentane, hexane, heptane, cyclopentane, methylcyclopentane, cyclohexane, etc. Following the addition of the catalyst and starting material, the apparatus is sealed, flushed with an inert gas such as nitrogen, and pressurized to the desired operating pressure with carbon monoxide and hydrogen. Upon reaching the desired operating pressure, the apparatus is then heated to a predetermined operating temperature and maintained thereat for the desired residence time which may range from about 0.5 up to about 10 hours or more in duration. Upon completion of the desired residence time, heating is discontinued and, after the apparatus and contents thereof have returned to room temperature, the excess pressure is discharged, the apparatus is opened, and the reaction mixture is recovered therefrom. After separation of the product mix from the catalyst, the former may then be subjected to conventional means of separating the components of said mix, said means including fractional distillation, fractional crystallization, etc.

It is also contemplated within the scope of this invention that the alkylation of the alkylamine compound may be accomplished in a continuous manner of operation. When such a type of operation is employed, the starting material comprising the alkylamine containing at least two alkyl substituents is continuously charged to an apparatus which is maintained at the proper operating conditions of temperature and pressure. In addition, the catalyst which is to be employed as well as any solvent is also continuously charged to the reaction apparatus either through separate lines or, if so desired, the components of the reaction mixture may be admixed prior to entry into the reaction apparatus and the resulting mixture charged thereto in a single stream. After passage through the apparatus for a predetermined period of time, the reactor effluent is continuously withdrawn and subjected to conventional means of separation whereby the product mix is separated from the catalyst and any unreacted starting material that is to be recycled to the reaction apparatus to form a portion of the feedstock, while the product mix is subjected to further distillation to recover the various components of said mix.

The following examples are given for purposes of illustrating the process of this invention. However, it is to be understood that these examples are given merely for purposes of illustration and that the present process is not necessarily limited thereto.

EXAMPLE I

To an 850 cc stainless steel rotating autoclave was added 14.0 grams of triethylamine, 1.0 gram of dicobalt octacarbonyl, and 10 grams of an undecane solvent, the molar ratio of triethylamine to cobalt being 23.2:1. The autoclave was sealed and flushed with nitrogen, following which the autoclave was pressurized to 150 atmospheres with a 1:1 carbon monoxide-hydrogen gas mixture. Thereafter, the autoclave was then heated to a temperature of 150° C. and maintained thereat for a period of 3 hours. At the end of this period, heating was discontinued and the autoclave was allowed to return to room temperature. The excess pressure was discharged, the autoclave was opened, and the reaction product comprising a red liquid was recovered. The product was analyzed by means of gas liquid chromatography and mass spectroscopy. This analysis determined that there had been a 32.0% conversion of the triethylamine, while the selectivity of the product mix is set forth in Table I below.

TABLE I

| Alkylated Product | Percent |
|---|---|
| butyldiethylamine | 13.8 |
| hexyldiethylamine | 14.7 |
| octyldiethylamine | 28.8 |
| decyldiethylamine | 20.4 |
| dodecyldiethylamine | 10.9 |

EXAMPLE II

In a manner similar to that set forth in Example I above, 16.6 grams of triethylamine, 0.70 gram of tetracobalt dodecacarbonyl and 10 grams of solvent were placed in a pyrex liner of a stainless steel rotating autoclave. The autoclave was sealed, flushed with nitrogen and pressurized to 150 atmospheres with a 1:1 carbon monoxide-hydrogen gas mixture. The autoclave was heated to a temperature of 150° C. and maintained thereat for a period of 3 hours. At the end of this period, heating was discontinued, the autoclave was allowed to return to room temperature and, after the excess pressure was discharged, the autoclave was opened. The reaction product comprising a red liquid was recovered and analyzed by gas liquid chromatography and mass spectroscopy. The results of this analysis which showed a 34.6% conversion of the triethylamine is set forth in Table II below.

TABLE II

| Alkylated Product | Percent |
|---|---|
| butyldiethylamine | 13.3 |
| hexyldiethylamine | 12.0 |
| octyldiethylamine | 27.1 |
| decyldiethylamine | 32.2 |
| dodecyldiethylamine | 15.4 |

EXAMPLE III

In a manner similar to that set forth in the above examples, di- and tri-substituted amines such as dibutylamine, dipropylamine and diethylamine may be subjected to alkylation in the presence of a catalyst such as rhodium carbonyl chloride utilizing similar reaction conditions of temperature and pressure to produce alkylated products which may include such compounds as octyldibutylamine, dodecyldibutylamine, hexadecyldibutylamine, hexylpropylamine, nonylpropylamine, dodecylpropylamine, pentadecylpropylamine, butylethylamine, hexylethylamine, octylethylamine, decylethylamine, and dodecylethylamine.

I claim as my invention:

1. A process for the self-alkylation of an amine compound which comprises reacting a reactant material consisting of an amine compound containing at least two alkyl substituents at alkylation conditions in the presence of a cobalt carbonyl, a rhodium carbonyl, or a cobalt or rhodium containing compound which is capable of forming a carbonyl under alkylation conditions, and recovering the resultant alkylated amine product.

2. The process as set forth in claim 1 in which said alkylation conditions include a temperature in the range of from about 50° C. to about 300° C. and a pressure in the range of from about 20 to about 300 atmospheres.

3. The process as set forth in claim 2 further characterized in that said pressure is effected by the presence of a carbon monoxide and hydrogen atmosphere.

4. The process as set forth in claim 1 in which said alkyl substituent of said amine contains from about 2 to about 6 carbon atoms.

5. The process as set forth in claim 1 in which said cobalt compound comprises dicobalt octacarbonyl.

6. The process as set forth in claim 1 in which said cobalt compound comprises tetracobalt dodecacarbonyl.

7. The process as set forth in claim 1 in which said rhodium compound comprises rhodium carbonyl chloride.

8. The process as set forth in claim 1 in which said amine compound is triethylamine and said alkylated amine product is a mixture of butyldiethylamine, hexyldiethylamine, octyldiethylamine, decyldiethylamine and dodecyldiethylamine.

9. The process as set forth in claim 1 in which said amine compound is tributylamine and said alkylated amine product is a mixture of octyldibutylamine, dodecyldibutylamine, and hexadecyldibutylamine.

10. The process as set forth in claim 1 in which said amine compound is dipropylamine and said alkylated amine product is a mixture of hexylpropylamine, nonylpropylamine, dodecylpropylamine and pentadecylpropylamine.

11. The process as set forth in claim 1 in which said amine compound is diethylamine and said alkylated amine product is a mixture of butylethylamine, hexylethylamine, octylethylamine, decylethylamine, and dodecylethylamine.

* * * * *